United States Patent [19]

Landscheidt et al.

[11] Patent Number: 5,744,663
[45] Date of Patent: Apr. 28, 1998

[54] PROCESS FOR PREPARING CYCLOPENTYL BROMIDE

[75] Inventors: Heinz Landscheidt, Duisburg; Alexander Klausener, Köln; Matthias Stenger, Monheim; Paul Wagner, Düsseldorf, all of Germany

[73] Assignee: Bayer Aktiengesellschaft, Leverkusen, Germany

[21] Appl. No.: 676,027

[22] Filed: Jul. 5, 1996

[30] Foreign Application Priority Data

Jul. 12, 1995 [DE] Germany ............... 195 25 356.6
Feb. 14, 1996 [DE] Germany ............... 196 05 402.8

[51] Int. Cl.$^6$ .................................................. C07C 21/00
[52] U.S. Cl. ................................. 570/250; 570/248
[58] Field of Search ................................. 570/248, 250

[56] References Cited

U.S. PATENT DOCUMENTS 3,763,250 10/1973 Rai et al. .
3,812,212 5/1974 Gordon .

FOREIGN PATENT DOCUMENTS 3031228 2/1991 Japan ..................... 570/248
1180037 2/1970 United Kingdom .

OTHER PUBLICATIONS

Ionic Chlorination (Bromination of Alkanes and Cycloalkanes with Methylene Chloride (Bromide)/Antimony Pentfluoride[1], Olah et al, J. Org. Chem., 54, 1463–1465 (1989).

A Synthetic Procedure for Secondary Bromides from Alcohols, Jenkins et al, J. Org. Chem., 27, 624–625 (1962).

Noller et al, J. Am. Chem. Soc., 48, 1084–1085 (1926).

Higher Hydrocarbons.[1] II. Five 11–Substituted Heneicosanes, Whitmore et al, J. Am. Chem. Soc., 64, 1801–1802 (1942).

Organoboranes for Synthesis . . . via Hydroboration, Tetrahedron vol. 44, No. 10, pp. 2763–2772 (1988).

*Primary Examiner*—Alan Siegel
*Attorney, Agent, or Firm*—Sprung Kramer Schaefer & Briscoe

[57] ABSTRACT

It has been found that cyclopentene and hydrogen bromide can be continuously reacted in a simple manner to give cyclopentyl bromide in good yields and good selectivities if the reaction is carried out in the presence of a heterogeneous catalyst. The reaction can be carried out continuously and unreacted cyclopentene and possibly other constituents can be recirculated to the reaction.

8 Claims, No Drawings

PROCESS FOR PREPARING CYCLOPENTYL BROMIDE

The present invention relates to a continuous process for preparing cyclopentyl bromide by reacting cyclopentene with hydrogen bromide.

Cyclopentyl bromide is used especially as alkylating reagent for introducing the cyclopentyl radical. For example, pharmaceuticals and agrochemicals are prepared in this way. EP-A 1 414 019 describes lipoxygenase inhibitors and EP-A 1 635 485 describes herbicides for whose preparation cyclopentyl bromide is used in each case.

The literature has disclosed only a few processes for preparing cyclopentyl bromide. It is evident that the synthesis of this compound presents certain problems. Thus, according to J. Org. Chem. 27, 624 to 625 (1962), the ester obtainable by reacting p-toluenesulphonic chloride with cyclopentanol can be reacted with calcium bromide to form cyclopentyl bromide.

According to J. Am. Chem. Soc. 48, 1084 (1926), cyclopentanol can be converted into cyclopentyl bromide by reaction with phosphorus tribromide.

The direct reaction of cyclopentanol with hydrogen bromide to give cyclopentyl bromide has also been described (J. Am. Chem. Soc. 64, 1801 to 1802 (1942)), but only in a yield of 70% of theory.

All these processes have in common that the starting material is the comparatively expensive cyclopentanol.

Mention may be made of the following processes which start from cheaper and more readily available starting materials such as cyclopentane or cyclopentene: The reaction of cyclopentane with methylene bromide and antimony pentafluoride (J. Org. Chem. 54, 1643 (1989)) and the hydroboration of cyclopentene and cleavage of the intermediate tricyclopentylborane with bromine (Tetrahedron 40, 2763 to 2784 (1988)).

However, both these processes are unsuitable for an industrial reaction since expensive reagents have to be used and large amounts of by-products and waste materials are obtained, these requiring considerable outlay for disposal.

In principle, it should also be possible to react cyclopentene directly with hydrogen bromide. However, the literature gives no usable examples of this reaction. Rather, in the case of the conditions which come into question, undesired secondary reactions, for example polymerizations, have to be expected to a considerable extent (see Houben-Weyl, Volume 5/4, page 103 (1960)).

There was therefore the object of finding an economical process for preparing cyclopentyl bromide.

It has now been found that cyclopentene can be reacted continuously with hydrogen bromide to give cyclopentyl bromide if the reaction is carried out in the presence of a heterogeneous catalyst.

It has further been found that the process of the invention is advantageously carried out by separating cyclopentyl bromide from the reaction mixture and recirculating the other components of the reaction mixture, essentially unreacted cyclopentene, to the reaction. This method of operation has no conspicuously adverse consequences in respect of conversion, yield and catalyst life and is particularly suitable for a continuous procedure.

In the process of the invention, the starting materials (cyclopentene and hydrogen bromide) can be passed in pure or diluted form and in a condensed, partially condensed or gaseous state over the catalyst. The reaction products can, particularly when working in the gas phase, be separated from the product stream, for example by condensation.

In a preferred embodiment of the process of the invention, cyclopentene is introduced in vapour form into the reaction zone together with an inert gas stream, e.g. nitrogen, carbon dioxide or argon, and with feeding in of hydrogen bromide and a recirculated proportion of cyclopentene.

In a further preferred embodiment of the process of the invention, cyclopentene, optionally in the presence of a diluent which is stable under reaction conditions, is reacted in condensed form, for example in the form of a trickling phase reaction, with hydrogen bromide, with the metering in of the hydrogen bromide being able to be carried out in cocurrent or in countercurrent to cyclopentene.

The reaction according to the invention of cyclopentene with hydrogen bromide can be carried out, for example, at temperatures between −20 and +300° C., preferably between 0 and 150° C. and particularly preferably between 10 and 110° C., and, for example, at pressures between 0.01 and 30 bar, preferably between 0.1 and 10 bar, particularly preferably between 0.5 and 5 bar and very particularly preferably between 0.8 and 1.5 bar.

Suitable heterogeneous catalysts for the process of the invention are, for example, metal compounds which are applied to support materials. It is also possible to use agglomerated, shaped or unshaped solid bodies which can be obtained by mixing of metal compounds with formative components for support materials and subsequent mechanical treatment or shaping. Such production processes are fundamentally known to those skilled in the art.

Suitable metal compounds are, in particular, metal salts, e.g. those of copper, iron, cobalt, nickel, chromium, bismuth, zinc, cadmium, vanadium, tungsten, mercury, antimony, aluminium and/or molybdenum. Preference is given to the salts of inorganic acids such as fluorides, chlorides, bromides, sulphates and/or phosphates of the metals specified. In principle, it is also possible to produce the catalysts of the invention using metal salts derived from organic acids. Such catalysts are generally converted into the corresponding bromides under the reaction conditions.

Suitable support materials are, for example, activated carbon, silica gel, silicon dioxide, silicic acids, aluminium oxide, oxides and phosphates of the rare earth metals, zeolites, aluminosilicates, solid heteropolyacids such as niobium heteropolyacids and ceramic bodies.

The catalyst can be produced, for example, by one of the following methods:

a) One or more metal salts are dissolved in a solvent, e.g. water, and a support material is impregnated with the solution and dried.

b) A metal salt solution is prepared as in a) and this is applied to a support material by adsorption.

c) One or more metal salts, if desired auxiliaries and one or more formative components for support materials are mixed and this mixture is converted into agglomerated, shaped or unshaped solid bodies, for example into extrudates, cylinders, spheres, ellipsoids or granules. If desired, a heat treatment can follow.

Based on 1 mol of cyclopentene, it is possible to use, for example, from 0.05 to 5 mol of hydrogen bromide. This amount is preferably from 0.1 to 2 mol.

The reaction mixture present after the reaction according to the invention can be worked up, for example, as follows: If the reaction has been carried out at elevated temperatures, the components condensable at, for example, 0° C. or lower temperatures, are first condensed. The condensate thus obtained can then be fractionated, for example, by distillation. This generally gives cyclopentyl bromide in conversions of over 45% and in selectivities of over 80%. Unreacted cyclopentene present in the reaction mixture can also be separated off in this manner (it then generally remains in the gas phase) and recirculated to the process. Any unreacted hydrogen bromide present in the reaction mixture can be removed before or after the condensation by means of scrubbing, for example with water.

The process of the invention can be carried out, for example, at a gas hourly space velocity over the catalyst of from 100 to 10 000 $h^{-1}$, preferably from 200 to 5 000 $h^{-1}$.

The reaction mixture is preferably worked up by feeding the reaction mixture leaving the reactor, e.g. a tube bundle reactor, to a separation apparatus in which cyclopentyl bromide is separated off. The separation apparatus can be, for example, a distillation column in which cyclopentyl bromide is separated off as bottom product. The gas phase obtained at the top of the column can be fed to a condenser. The condensate obtained there can be partly recirculated as runback to the upper part of the distillation column and partly recirculated to the reactor. The gas phase leaving the condenser is recirculated to the reactor, with it being possible to bleed off a small part thereof and thus take by-products from the process.

In a particularly preferred, continuous embodiment of the process of the invention, the procedure is as follows: The reactor is operated at temperatures in the range from 20 to 100° C. and at pressures in the range from 0.5 to 5 bar. It is fed with a mixture containing, for example, from 5 to 15% by weight of cyclopentene, from 60 to 90% by weight of inert gas, from 2 to 10% by weight of hydrogen bromide, from 0 to 10% by weight of cyclopentyl bromide and from 0 to 10% by weight of low-boiling by-products recirculated together with cyclopentene. The reaction mixture leaving the reactor is fed to a distillation column which is operated in such a way that a gaseous top product containing from 0.1 to 10% by weight of cyclopentene, from 65 to 95% by weight of inert gas, from 0 to 5% by weight of hydrogen bromide, from 5 to 20% by weight of cyclopentyl bromide and from 0 to 10% by weight of volatile by-products can be taken off at temperatures in the range from 0 to 100° C. at pressures in the range from 0.5 to 5 bar, and a liquid bottom product containing at least 95% by weight of cyclopentyl bromide can be taken off at temperatures in the range from 50 to 200° C. The gaseous top product is cooled and a condensate having a temperature of from −50 to +50° C. is thus obtained, this condensate containing from 1 to 80% by weight of cyclopentene, from 10 to 95% by weight of cyclopentyl bromide, from 0 to 5% by weight of hydrogen bromide and from 0 to 50% by weight of by-products. This condensate is divided into two substreams in a ratio of from 10:1 to 1:10. Of these substreams, one is recirculated as runback to the upper part of the distillation column and the other is recirculated to the reaction. The gas phase remaining after cooling the top product of the distillation column contains from 75 to 95% by weight of inert gas, from 0 to 15% by weight of cyclopentene, from 0 to 5% by weight of hydrogen bromide, from 0 to 15% by weight of cyclopentyl bromide and from 0 to 10% by weight of by-products. From this gas phase, a proportion of from 0.5 to 10% by weight is bled off, the remainder is recirculated to the reaction.

The process of the invention has the advantages that it starts from simple, inexpensive and readily available starting materials, gives cyclopentyl bromide in good yields and selectivities, no particular ecological measures are necessary and few unusable by-products (e.g. polymers) are obtained. It can also be carried out continuously with good results and in a very economical manner.

EXAMPLES

Example 1

100 g of lanthanum phosphate in the form of granules were impregnated with a solution of 10 g of copper(II) chloride in 50 ml of water. The catalyst thus obtained was dried in vacuo at a temperature of 35° C.

20 ml of the catalyst thus obtained were placed in the middle of a glass tube having an internal diameter of 3 cm and otherwise filled with glass Raschig rings.

A stream of nitrogen of 5 standard l/h was passed continuously through a gas wash bottle containing cyclopentene and the gas stream saturated in this way with cyclopentene was, after continuously mixing in gaseous hydrogen bromide (4 g/h), passed at 40° C. over the catalyst.

The reaction product obtained at the outlet of the glass tube was condensed by cooling to −10° C. A sample of the condensate was washed with dilute sodium hydrogen carbonate solution and analysed by gas chromatography. The conversion based on cyclopentene used was 50%, the selectivity based on cyclopentene used was 90%.

Example 2

The catalyst and the reaction vessel were as in Example 1.

Liquid cyclopentene (12 g/h) and gaseous hydrogen bromide (4 g/h) were fed continuously into the glass tube by means of a pump. The temperature of the catalyst was 50° C.

The work-up and analysis were carried out as in Example 1. The conversion was 80% and the selectivity was 85%.

Example 3

Using flowsheeting simulation a design of the process in a technical scale is derived as follows:

350 l of a catalyst produced using a method similar to Example 1 are introduced into a tube bundle reactor (dimensions: length 3000 mm and diameter 300 mm) containing 109 individual tubes each having a diameter of 37 mm and a wall thickness of 6.5 mm. A cooling fluid maintained at 30° C. flows through the jacket space of the reactor.

309 kg/h of a mixture containing 8.8% by weight of cyclopentene, 5.8% by weight of hydrogen bromide, 2.2% by weight of cyclopentyl bromide, 81.3% by weight of nitrogen and 1.9% by weight of cyclopentane and heated to 40° C. are fed to the reactor at atmospheric pressure.

The gas stream leaving the reactor has a temperature of 40° C. and is introduced into a column (length: 3300 mm, diameter: 300 mm). At the top of the column there is fitted a heat exchanger which is regulated by cooling with brine in such a way that the gas exiting the condenser and the liquid flowing from the condenser each has a temperature of −10° C. The gas leaving the condenser contains 4.7% by weight of cyclopentene, 0.7% by weight of hydrogen bromide, 1.0% by weight of cyclopentyl bromide, 91.7% by weight of nitrogen and 2.0% by weight of cyclopentane and the liquid flowing from the condenser contains 10.6% by weight of cyclopentene, 83.7% by weight of cyclopentyl bromide and 5.6% by weight of cyclopentane. The gas is warmed to a temperature of 25° C. and 0.65% by weight thereof (1.7 kg/h) is continuously bled off and disposed of. The remaining gas stream is recirculated to the reaction.

The bottom stream leaving the column (30 kg/h) has a temperature of 130° C and contains 99% by weight of cyclopentyl bromide.

The liquid flowing from the condenser is divided into two substreams of which one is recirculated as runback to the upper region of the column and the other is recirculated to the reaction. The weight ratio of the said substreams is 6:1 (runback to the column: recirculation to the reaction).

The reaction product thus obtained, viz. cyclopentyl bromide, is suitable without further purification for further reactions, for instance alkylations.

What is claimed is:

1. A substantially gaseous or gaseous process for the continuous preparation of cyclopentyl bromide from cyclopentene and hydrogen bromide, in which the reaction is carried out in the presence of a heterogeneous catalyst comprising passing the starting materials cyclopentene and hydrogen bromide in pure or diluted form in a substantially gaseous or gaseous state over the heterogeneous catalyst.

2. The process of claim 1, in which the reaction is carried out at temperatures between −20° and +300° C. and at pressures between 0.01 and 30 bar.

3. The process of claim 1, in which the catalyst used comprises a metal compound on a support material.

4. The process of claim 3, in which salts of copper, iron, cobalt, nickel, chromium, bismuth, zinc, cadmium, vanadium, tungsten, mercury, antimony, aluminium and/or molybdenum are used as catalyst and activated carbon, silica gel, silicon dioxide, silicic acids, aluminium oxide, oxides and/or phosphates of the rare earth metals, zeolites, aluminosilicates, solid heteropolyacids or ceramic bodies are used as support material.

5. The process of claim 1, in which from 0.05 to 5 mol of hydrogen bromide is used per 1 mol of cyclopentene.

6. The process of claim 1, in which the reaction mixture present after the reaction is worked up by first condensing the components condensable at 0° C. or less and recirculating unreacted cyclopentene to the process.

7. The process of claim 1, in which the reaction mixture after reaction is fed to a distillation column in which cyclopentyl bromide is separated off as bottom product, the gas phase obtained at the top of the column is fed to a condenser, the condensate so obtained is partly recirculated to the reactor and the gas phase leaving the condenser is recirculated to the reactor, with a small part thereof being bled off.

8. A gaseous process for the continuous preparation of cyclopentyl bromide from cyclopentene and hydrogen bromide, in which the reaction is carried out in the presence of a heterogeneous catalyst comprising passing the starting materials cyclopentene and hydrogen bromide in pure or diluted form in a gaseous state over the heterogeneous catalyst.

* * * * *